(12) United States Patent
Takeuchi et al.

(10) Patent No.: US 6,303,357 B1
(45) Date of Patent: Oct. 16, 2001

(54) L-α-GLYCEROPHOSPHATE OXIDASE GENE, RECOMBINANT DNA, AND METHOD FOR PRODUCING MODIFIED L-α-GLYCEROPHOSPHATE OXIDASE GENE

(75) Inventors: Kenichi Takeuchi; Yoshinao Koide; Yuji Nakanishi, all of Aichi; Satoru Suzuki, Gifu, all of (JP)

(73) Assignee: Amano Pharmaceutical Co., Ltd., Aichi (JP)

( * ) Notice: Subject to any disclaimer, the term of this patent is extended or adjusted under 35 U.S.C. 154(b) by 0 days.

(21) Appl. No.: 09/537,682

(22) Filed: Mar. 29, 2000

(51) Int. Cl.⁷ ............................. C12N 9/04; C12N 15/00; C12N 1/20; C12P 21/04; C07H 21/04
(52) U.S. Cl. ..................... 435/190; 435/71.2; 435/252.3; 435/440; 536/23.2
(58) Field of Search .................................. 435/190, 71.2, 435/440, 252.3; 536/23.2, 23.7

(56) References Cited

U.S. PATENT DOCUMENTS 4,960,877 * 10/1990 Sagai et al. ............................. 536/27

FOREIGN PATENT DOCUMENTS

| 38 42 090 A1 | 7/1989 | (DE) . |
| A-10-150985 | 6/1998 | (JP) . |

OTHER PUBLICATIONS

Parsonage et al. The Journal of Biological Chemistry, vol. 273, No. 37, pp. 23812–23822. (Sep. 1998).*
Matsuoka et al. JP10150985–A. Sep. 1998. (English translation).*
Journal of Bacteriology, pp. 1063–1068 (Jun., 1969).*
European Search Report.

* cited by examiner

Primary Examiner—Ponnathapu Achutamurthy
Assistant Examiner—Yong Pak
(74) Attorney, Agent, or Firm—Sughrue, Mion, Zinn, Macpeak & Seas, PLLC

(57) ABSTRACT

This invention provides an L-α-glycerophosphate oxidase (GPO) having excellent properties such as stability, heat resistance and reactivity. A recombinant GPO obtained by replacing an amino acid of a specified position of an amino acid sequence deduced from the *Enterococcus faecium* No. 7044 GPO gene or DNA coding for the GPO with other amino acid has excellent thermal stability and reactivity. That is, the invention provides modified forms of the GPO having the amino acid sequence of Sequence No. 1 in the Sequence Listing, in which the 130-position leucine counting from the N-terminus of the GPO is replaced by other amino acid and/or the 225-position serine counting from the N-terminus of the GPO is replaced by other amino acid and/or the 298-position threonine counting from the N-terminus of the GPO is replaced by other amino acid and/or the 420-position aspartic acid counting from the N-terminus of the GPO is replaced by other amino acid.

11 Claims, No Drawings

SEQUENCE LISTING

```
<160> NUMBER OF SEQ ID NOS: 2

<210> SEQ ID NO 1
<211> LENGTH: 607
<212> TYPE: PRT
<213> ORGANISM: Enterococcus faecium No. 7044

<400> SEQUENCE: 1

Met Phe Ser Asn Lys Thr Arg Gln Asp Ser Ile Gln Lys Met Gln Gln
 1               5                  10                  15

Glu Glu Leu Asp Leu Leu Ile Ile Gly Gly Gly Ile Thr Gly Ala Gly
                20                  25                  30

Val Ala Val Gln Ala Ala Ala Ser Gly Ile Lys Thr Gly Leu Ile Glu
            35                  40                  45

Met Gln Asp Phe Ala Glu Gly Thr Ser Ser Arg Ser Thr Lys Leu Val
        50                  55                  60

His Gly Gly Ile Arg Tyr Leu Lys Thr Phe Asp Val Glu Val Val Ala
 65                  70                  75                  80

Asp Thr Val Gly Glu Arg Ala Val Val Gln Gly Ile Ala Pro His Ile
                85                  90                  95

Pro Lys Pro Asp Pro Met Leu Leu Pro Ile Tyr Glu Asp Glu Gly Ala
                100                 105                 110

Thr Thr Phe Asn Met Phe Ser Val Lys Val Ala Met Asp Leu Tyr Asp
            115                 120                 125

Lys Leu Ala Asn Val Thr Gly Thr Lys Tyr Glu Asn Tyr Thr Leu Thr
    130                 135                 140
```

-continued

```
Pro Glu Val Leu Glu Arg Glu Pro Phe Lys Lys Gly Leu
145                 150                 155                 160

Lys Gly Ala Gly Val Tyr Leu Asp Phe Arg Asn Asp Ala Arg Leu
            165                 170                 175

Val Ile Asp Asn Ile Lys Lys Ala Ala Glu Asp Gly Ala Tyr Leu Val
            180                 185                 190

Ser Lys Met Lys Ala Val Gly Phe Leu Tyr Glu Gly Asp Gln Ile Val
        195                 200                 205

Gly Val Lys Ala Arg Asp Leu Leu Thr Asp Glu Val Ile Glu Ile Lys
    210                 215                 220

Ser Lys Leu Val Ile Asn Thr Ser Gly Pro Trp Val Asp Lys Val Arg
225                 230                 235                 240

Asn Leu Asn Phe Thr Arg Pro Val Ser Pro Lys Met Arg Pro Thr Lys
            245                 250                 255

Gly Ile His Leu Val Val Asp Ala Lys Lys Leu Pro Val Pro Gln Pro
            260                 265                 270

Thr Tyr Phe Asp Thr Gly Lys Gln Asp Gly Arg Met Val Phe Ala Ile
        275                 280                 285

Pro Arg Glu Asn Lys Thr Tyr Phe Gly Thr Thr Asp Thr Asp Tyr Gln
    290                 295                 300

Gly Asp Phe Thr Asp Pro Lys Val Thr Gln Asp Val Asp Tyr Leu
305                 310                 315                 320

Leu Asp Val Ile Asn His Arg Tyr Pro Glu Ala Asn Ile Thr Leu Ala
            325                 330                 335

Asp Ile Glu Ala Ser Trp Ala Gly Leu Arg Pro Leu Leu Ile Gly Asn
        340                 345                 350

Ser Gly Ser Asp Tyr Asn Gly Gly Asp Asn Gly Ser Ile Ser Asp Lys
        355                 360                 365

Ser Phe Asn Lys Val Val Asp Thr Val Ser Glu Tyr Lys Glu Asn Lys
        370                 375                 380

Val Ser Arg Ala Glu Val Glu Asp Val Leu Asn His Leu Glu Asn Ser
385                 390                 395                 400

Arg Asp Glu Lys Ala Pro Ser Thr Ile Ser Arg Gly Ser Ser Leu Glu
            405                 410                 415

Arg Glu Pro Asp Gly Leu Leu Thr Leu Ser Gly Gly Lys Ile Thr Asp
            420                 425                 430

Tyr Arg Lys Met Ala Glu Gly Ala Leu Arg Leu Ile Arg Gln Leu Leu
        435                 440                 445

Lys Glu Glu Tyr Gly Ile Glu Thr Lys Glu Ile Asp Ser Lys Lys Tyr
    450                 455                 460

Gln Ile Ser Gly Gly Asn Phe Asp Pro Thr Lys Leu Glu Glu Thr Val
465                 470                 475                 480

Thr Glu Leu Ala Lys Glu Gly Val Ala Ala Gly Leu Glu Glu Asp
            485                 490                 495

Ala Thr Tyr Ile Ala Asp Phe Tyr Gly Thr Asn Ala Arg Arg Ile Phe
            500                 505                 510

Glu Leu Ala Lys Glu Met Ala Pro Tyr His Gly Leu Ser Leu Ala Glu
        515                 520                 525

Ser Ala Arg Leu Arg Tyr Gly Leu Glu Glu Met Val Leu Ala Pro
        530                 535                 540

Gly Asp Tyr Leu Ile Arg Arg Thr Asn His Leu Leu Phe Glu Arg Asp
545                 550                 555                 560

Gln Leu Asp Glu Ile Lys Gln Pro Val Ile Asp Ala Ile Ala Gly Tyr
```

| | 565 | | | 570 | | | 575 | | | | |
|---|---|---|---|---|---|---|---|---|---|---|---|
| Phe | Gly | Trp | Thr | Glu | Glu | Lys | Ala | Gln | Gln | Thr | Lys | Arg | Leu | Glu |
| | | | 580 | | | | 585 | | | | 590 |

| Ala | Leu | Ile | Ala | Glu | Ser | Asp | Leu | Arg | Glu | Leu | Lys | Gly | Glu | Lys |
|---|---|---|---|---|---|---|---|---|---|---|---|---|---|---|
| | | | 595 | | | | 600 | | | | 605 |

<210> SEQ ID NO 2
<211> LENGTH: 1821
<212> TYPE: DNA
<213> ORGANISM: Enterococcus faecium No. 7044

<400> SEQUENCE: 2

| | |
|---|---|
| atgtttcaa acaagacaag acaagatagc attcaaaaaa tgcagcaaga agaattggat | 60 |
| ctgttgatca tcggtggcgg aatcactggt gccggtgtag cagtccaggc agcagcatca | 120 |
| ggaatcaaaa caggattgat cgaaatgcaa gattttgcag aagggacgtc ctctcgctcg | 180 |
| accaaacttg tgcatggcgg tattcgttat ctgaaaacat ttgatgtgga agtagtagct | 240 |
| gacacagttg gtgaacgtgc agtcgtacaa ggtattgccc cacacattcc aaaaccagat | 300 |
| ccaatgcttt taccaatcta tgaagatgaa ggagcaacaa ccttcaatat gttctctgtc | 360 |
| aaagtagcaa tggacccttta cgacaaactc gcaaatgtga caggaactaa atatgagaac | 420 |
| tataccctga caccagaaga agtattggaa agagaaccat ttttgaaaaa agaagggcta | 480 |
| aaaggtgcag gtgtttatct ggatttccgc aacaatgatg cccgtttagt gatcgataat | 540 |
| atcaaaaagg ctgcagaaga tggggcttat ctagtaagta aaatgaaagc ggttggcttc | 600 |
| ttatatgagg gcgatcaaat cgttggcgtc aaagctcgtg atctgctgac agatgaagtg | 660 |
| atcgagatca aatcaaaatt agtgatcaat acgagtggtc cttgggtaga taagtaagg | 720 |
| aacttgaatt ttacgcgtcc agtctctcct aaaatgcgtc caaccaaagg gatccattta | 780 |
| gtcgtagatg cgaaaaaact gcctgtaccg caacccacgt acttcgatac aggaaaacaa | 840 |
| gatgggcgga tggtttttgc tatcccaaga gaaaacaaga cttactttgg tacgacagat | 900 |
| acggattacc aaggagactt tacgatcca aagtcacac aagaagacgt ggattatcta | 960 |
| ttggatgtga tcaatcatcg ctacccagaa gcaaatatca cattggcaga tatcgaagca | 1020 |
| agctgggcag gacttcgtcc gctattgatt ggtaattctg gttctgatta taatggtgga | 1080 |
| gataatggat cgatttcaga caagagcttc aataaagtgg ttgatacagt aagtgaatat | 1140 |
| aaggaaaata agtttctcg tgctgaagta gaagatgtgt tgaaccattt ggaaaacagc | 1200 |
| cgtgatgaaa aagcaccttc tacgatttcc agaggtagtt ctttagaaag agaaccagat | 1260 |
| ggcttgttga ctttatcagg tgggaaaatc actgattacc gtaagatggc agaaggagct | 1320 |
| ttacgattga ttcgtcagct gttaaaagaa gaatacggaa tagagacgaa agaaatcgat | 1380 |
| tctaaaaaat atcagatttc aggtggaaat ttcgatccaa cgaaattaga agaaacagtg | 1440 |
| acagaattag caaaagaagg agtagcagcc ggtttagagg aagaagatgc tacttatatc | 1500 |
| gctgattttt acgggactaa tgctcgacgt atctttgaat tagcaaaaga aatggcacct | 1560 |
| tatcatggct tgagtctcgc tgagtcagct cggttacgtt atggcttaga agaagaaatg | 1620 |
| gtttagctc caggtgatta tctcattcgt cgtacgaatc atctgttgtt tgaacgagat | 1680 |
| cagctggatg agatcaagca acctgtgatc gatgcaattg ctgggtattt tgggtggaca | 1740 |
| gaagaggaga aggcgcaaca gactaaacgt ttagaagcat tgatcgcaga atcagatctg | 1800 |
| cgggaactaa agggggagaa a | 1821 |

L-α-GLYCEROPHOSPHATE OXIDASE GENE, RECOMBINANT DNA, AND METHOD FOR PRODUCING MODIFIED L-α-GLYCEROPHOSPHATE OXIDASE GENE

FIELD OF THE INVENTION

This invention relates to an L-α-glycerophosphate oxidase (to be referred to as GPO hereinafter) gene, a novel recombinant DNA, a modified GPO and a method for the production of GPO.

BACKGROUND ART

GPO is known as an enzyme which catalyses a reaction in which dihydroxyacetone phosphate and one molecule of hydrogen peroxide are formed from L-α-glycerophosphate and one molecule of oxygen.

So far, bacteria belonging to the genus Streptococcus, the genus Lactobacillus, the genus Pediococcus (JP-A-58-165789 and JP-A-57-198085; the term "JP-A" as used herein means an "unexamined published Japanese patent application"), the genus Leuconostoc and the genus Aerococcus (JP-A-55-15746) are known as microorganisms which produce GPO, and the GPO produced by these bacteria can be used as an enzyme for clinical inspection and reagent use, e.g., for the measurement of lipase activity and determination of triglyceride, glycerol, ATP and the like.

Production of GPO by these conventional GPO-producing bacteria has several problems. For example, when a GPO-producing bacterium belonging to the genus Streptococcus is used, it entails problems such as considerably high cost. Thus, in recent years, a method for the production of GPO by means of recombinant DNA techniques has been reported using a bacterium belonging to the genus Streptococcus (JP-A-2-454), and it is known that the GPO produced by this method can be used as an enzyme for the clinical inspection reagent.

However, in order to use GPO in the aforementioned field, great concern has been directed toward the development of GPO having more superior stability and excellent properties such as heat resistance and reactivity and the production of GPO with a low cost. That is, since shift over to liquid reagents is in progress in the recent field of clinical inspection, development of more stable GPO having higher reactivity and higher reliability is expected.

SUMMARY OF THE INVENTION

In view of the above, it therefore becomes an object of the invention to provide a novel GPO-producing bacterium and also to provide a GPO having an amino acid sequence which is different from that of the naturally existing GPO but still having the GPO activity, in which physicochemical properties of the enzyme are modified by genetic engineering techniques.

Accordingly, the invention provides a GPO-producing bacterium newly screened from a natural source and also provides a recombinant DNA which can be replicated, in which a recombinant DNA obtained by replacing an amino acid of a specified position of the amino acid sequence deduced from DNA coding for the GPO by other amino acid is integrated into a vector, as well as a transformant containing the recombinant DNA and a method for the production of GPO having modified properties, which uses the same.

DETAILED DESCRIPTION OF THE INVENTION

With the aim of solving the aforementioned problems, the inventors of this invention have conducted intensive studies and revealed nucleotide sequence of a DNA fragment coding for GPO using a newly screened GOP producing bacterium and subsequently succeeded in obtaining GPO having further improved properties by modifying an amino acid sequence deduced from the nucleotide sequence.

That is, the inventors have carried out screening of GPO-producing bacteria from a broad range of natural sources and found that a bacterial strain isolated from a soil sample produces a novel GPO.

Bacteriological properties of the strain isolated by the inventors were identified with reference to Bergey's Manual of Systematic Bacteriology, vol. 2 (1986).

(1) Morphology

Gram positive, sub-spherical to ovoid, single coccus or 2 to 8 linked cocci, no spore formation, no motility.

(2) Cultural Properties (Culturing on Trypto-Soy Agar Plate at 37° C. for 24 Hours)

Shape of colony: circular
Surface of colony: smooth
Periphery of colony: entire
Rise of colony: convex
Gloss of colony: opaque, glistening
Color of colony: white (3) Physiological Properties Growth at 10° C.: yes
Growth at 45° C.: yes
Growth at 6.5% NaCl: yes
Growth at pH 9.6: yes
Growth with 40% bile medium: yes
Temperature resistance (60° C., 30 min.): yes
Hydrolysis of;
   arginine: positive
   hippurate: negative
   esclin: positive
   gelatin: negative
   starch: negative
Reduction of;
   methylene blue: positive
   TTC [2,3,5-triphenyltetrazolium chloride (in the presence of 0.5% glucose)]: negative
   tellurite: positive
Formation of acid from; glycerol:
   weakly positive
   cellobiose: positive
   L-arabinose: positive
   maltose: positive
   ribose: positive
   lactose: positive
   adonitol: negative
   melibiose: positive
   glucose: positive
   sucrose: positive
   sorbose: negative
   trehalose: positive
   rhamnose: positive
   inulin: negative
   mannitol: positive
   melezitose: negative
   sorbitol: negative
   raffinose: weakly positive
   arbutin: positive
   soluble starch: weakly positive Assimilation of;
  pyruvic acid: negative
  citric acid: negative
  malic acid: negative
  arginine: negative
  serine: negative
Formation of yellow pigment (insoluble): no Sensitivity for; bacitracin: resistant
  optochin: resistant
Catalase: negative
Cytochrome oxidase: negative
Litmus milk: acidic, no coagulation, reduces litmus
Formation of gas from glucose: negative
VP test: positive
Hemolysis: negative to weakly α-hemolytic
Behavior on oxygen: facultative anaerobe
Urease: negative
SF medium: growth
Bile solubility: negative
Reduction of nitrate: negative
Gas formation from malic acid (in the presence of glucose): positive As shown in Table 1, this strain belongs to the genus Enterococcus, because it is a Gram positive facultative anaerobic coccus which forms a chain and does not form gas from glucose and, as is evident also from Table 2, these properties coincide with the definition of the genus Enterococcus.

TABLE 1

| Genus name | Arrangements | Gas (glucose) |
| --- | --- | --- |
| Staphylococcus | irregular clusters | |
| Stomatococcus | irregular clusters | |
| Enterococcus | chains, pairs | − |
| Leuconostoc | pairs, chains | + |

TABLE 1-continued

| Genus name | Arrangements | Gas (glucose) |
| --- | --- | --- |
| Pediococcus | tetrads | |
| Aerococcus | tetrads | |
| This strain | chains, pairs | − |

TABLE 2

| | Genus Enterococcus | GPO producer |
| --- | --- | --- |
| Shape of cell | ovoid | sub-spherical-ovoid |
| Linkage | single, 2 or short | single, 2 to 8 linkage |
| Gram staining | positive | positive |
| Spore | no formation | no formation |
| Motility | positive or negative | negative |
| Oxygen | facultative anaerobe | facultative anaerobe |
| Optimum growth temperature | about 35° C. | 32 to 45° C. |
| Growth at 10° C. and 45° C. | positive | positive |
| Temp. resistance (60° C., 30 min.) | positive | positive |
| Growth at 6.5% NaCl or pH 9.6 | positive | positive |
| Hydrolysis of pyridonyl-β-naphthylamide | positive | positive |
| Final main metabolite of glucose | L-lactic acid | not tested |

Also, as shown in Tables 3 and 4, this strain can grow at 10° C., 45° C., 6.5% sodium chloride and pH 9.6 and with 40% bile, so that it belongs to the group of enterococci.

TABLE 3

| | Pyogenic streptococci | | | | | Oral streptococci | | | | | | | | | This strain |
| --- | --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 | |
| Growth at 10° C. | − | d | − | + | − | − | − | − | − | − | − | − | − | − | + |
| Growth at 45° C. | − | − | − | − | − | d | d | d | d | d | d | d | d | d | + |
| Growth at 6.5% NaCl | − | d | − | − | − | − | − | − | − | − | − | d | d | − | + |
| Growth at pH 9.6 | − | − | − | − | − | − | − | − | − | − | − | − | − | − | + |
| Growth with 40% bile | − | d | − | − | − | d | d | − | d | d | d | d | d | NT | + |
| α-Hemolysis | − | − | − | + | + | d | + | + | − | − | − | − | − | − | −wk |
| β-Hemolysis | + | d | + | + | − | − | − | − | − | − | − | − | − | − | − |
| Arginine hydrolysis | + | + | + | NT | + | − | + | − | d | − | + | − | − | − | + |
| Hippurate hydrolysis | − | + | − | − | − | − | − | − | − | − | − | − | − | − | − |
| Esculin hydrolysis | d | − | d | + | d | + | d | − | d | + | + | d | + | + | + |

TABLE 4

|  | Enterococci | | | | Lactic strepto | | | Other streptococci | | | | This strain |
|---|---|---|---|---|---|---|---|---|---|---|---|---|
|  | 15 | 16 | 17 | 18 | 19 | 20 | 25 | 26 | 27 | 28 | 29 | + |
| Growth at 10° C. | + | + | + | + | − | − | − | + | − | − | − | + |
| Growth at 45° C. | + | + | + | + | − | − | − | − | d | + | + | + |
| Growth at 6.5% NaCl | + | + | + | + | − | − | NT | − | − | − | − | + |
| Growth at pH 9.6 | + | + | + | + | − | − | − | − | d | − | − | + |
| Growth with 40% bile | + | + | + | + | + | − | NT | d | + | + | − | + |
| α-Hemolysis | − | d | d | + | d | − | d | d | wk | wk | d | −wk |
| β-Hemolysis | + | − | − | − | − | − | − | − | − | − | − | − |
| Arginine hydrolysis | + | + |   | d | d | d | − | + | − | − | d | + |
| Hippurate hydrolysis | + | d |   | d | d | d | + | + | − | − | − | − |
| Esculin hydrolysis | + | + | + | + | d | + | − | + | + | + | − | + |

In the above tables, 1 is *S. pyogenes*, 5 is *S. pneumoniae*, 6 is *S. salivarius*, 15 is *E. faecalis*, 16 is *E. faecium* and 29 is *S. thermophilus*.

In addition, as shown in Table 5, examination of the classification of enterococci confirms that the strain of the invention is identified as *Enterococcus faecium* based on the reduction of methylene blue, hydrolysis of arginine, reduction of tellurite and formation of acid (from arabinose, arbutin, melezitose and melibiose).

TABLE 5

| Characteristics | E. faecalis | E. faecium | E. avium | E. gallinarm | This strain |
|---|---|---|---|---|---|
| 0.1% Methylene blue milk | + | + | d | − | + |
| Ammonia from arginine | + | + | − | d | + |
| Reduction of tetrazolium | + | − | − | + | − |
| Reduction of potassium tellurite | + | d | d | − | − |
| Tyrosine decarboxylated | + | − | ND | ND | / |
| Acid from L-arabinose | − | d | + | + | + |
| arbutin | − | + | + | + | + |
| melezitose | + | − | + | d | − |
| melibiose | − | + | d | + | + |
| sorbitol | + | d | + | + | − |
| sorbose | − | + | − | − | − |

The inventors have named this strain *Enterococcus faecium* No. 7044. This strain has been deposited at National Institute of Bioscience and Human Technology, 1-3, Higashi 1-chome, Tsukuba-shi, Ibaraki 305, JAPAN, from Mar. 21, 2000 under the accession number of FERM BP-7100.

As described in the foregoing, in order to use GPO more broadly as an enzyme reagent, it is necessary to improve its properties, particularly stability and reactivity. In general, enzyme chemical properties such as substrate specificity, optimum pH and physical stability of an enzyme are regulated by its amino acid sequence. Because higher order structure of a protein is based on its amino acid sequence, it is known that modification of the amino acid sequence is one method for modifying the protein.

In view of the above, the inventors have conducted intensive studies and found as a result of the efforts that a novel enzyme having more superior properties, in which enzyme chemical properties of GPO having the original sequence are modified, can be produced by modifying, by means of gene engineering techniques, at least one amino acid residue (preferably, from 1 to 10 amino acid residues, more preferably from 1 to 4 amino acid residues) in an amino acid sequence ranging from the N-terminus to the C-terminus of GPO produced by a newly screened bacterium belonging to the genus Enterococcus, *Enterococcus faecium* No. 7044, thereby accomplishing the invention.

That is, the inventors have prepared a transformant by transforming an *Escherichia coli* strain with the GPO gene of *Enterococcus faecium* No. 7044, modified the transformant in such a manner that it could produce a recombinant GPO in which an amino acid of a specified position of the amino acid sequence deduced from the DNA coding for the GPO is replaced by other amino acid, and succeeded in producing a GPO having excellent thermal stability and reactivity in comparison with the conventional GPO, in a cultured mixture of the resulting transformant, thus resulting in the accomplishment of the invention.

Thus, the present invention provides a polypeptide which comprises a polypeptide having an L-α-glycerophosphate oxidase activity and having the amino acid sequence of Sequence No. 1 in the Sequence Listing wherein one or more of amino acid residues of the amino acid sequence may be modified by at least one of deletion, addition, insertion and substitution.

The invention further provides modified forms of the GPO having the amino acid sequence of Sequence No. 1 in the Sequence Listing, in which the 130-position leucine counting from the N-terminus of the GPO is replaced by other amino acid and/or the 225-position serine counting from the N-terminus of the GPO is replaced by other amino acid and/or the 298-position threonine counting from the N-terminus of the GPO is replaced by other amino acid and/or the 420-position aspartic acid counting from the N-terminus of the GPO is replaced by other amino acid.

In these modified forms of GPO, their enzyme chemical properties are modified in various points in comparison with the original GPO. For example, affinity for substrate, specific activity and heat resistance are modified. In more illustratively describing, affinity for substrate is modified by replacing the 130-position leucine counting from the N-terminus of the GPO by other amino acid, specific activity is modified by replacing the 225-position serine counting from the N-terminus of the GPO by other amino acid, heat resistance is modified by replacing the 298-position threonine counting from the N-terminus of the GPO by other amino acid and heat resistance is also modified by replacing the 420-position aspartic acid counting from the N-terminus of the GPO by other amino acid.

When the aforementioned amino acid at each position is replaced, the amino acid to be replaced is not particularly limited, but the following combinations are preferably used.

The 130-position amino acid: leucine→phenylalanine, tryptophan
The 225-position amino acid: serine→alanine
The 298-position amino acid: threonine→proline
The 420-position amino acid: aspartic acid→glycine Introduction of mutation into the GPO gene can be carried out by a known method such as a chemical method which uses hydroxylamine hydrochloride, N-methyl-N'-nitro-N-nitrosoguanidine (NTG), nitrous acid, sulfurous acid, hydrazine, formic acid or 5-bromouracil, ultraviolet ray irradiation, error prone PCR (cf. J. C. Moore, F. H. Arnold., Nature Bioteck., 14, 458–467 (1996), herein incorporated by reference) or site-directed (site-specific) mutagenesis (cf. the oligonucleotide-directed Dual Amber method described in Hashimoto-Gotoh. T. et al. (1995), Gnene, 152, 271 et seq., herein incorporated by reference).

Examples of the gene which encodes the enzyme of the present invention include a gene which can be obtained from a microorganism capable of producing said enzyme by cloning of said gene and a gene which has a certain degree of homology of at least 60% or more, preferably a gene having a homology of 80% or more and more preferably a gene having a homology of 95% or more. The following polynucleotide (DNA or RNA) is desirable as the gene which encodes the enzyme of the present invention.

A nucleotide which comprises a nucleotide being selected from the following nucleotides (a) to (g) and encoding a polypeptide having an L-α-glycerophosphate oxidase activity;
(a) a nucleotide which encodes a polypeptide having the amino acid sequence of Sequence No. 1 shown in the Sequence Listing,
(b) a nucleotide which encodes a polypeptide having the amino acid sequence of Sequence No. 1 in the Sequence Listing, wherein one or more amino acid residues of the amino acid sequence are modified by at least one of deletion, addition, insertion and substitution,
(c) a nucleotide which has the nucleotide sequence of Sequence No. 2 in the Sequence Listing,
(d) a nucleotide which has the nucleotide sequence of Sequence No. 2 in the Sequence Listing, wherein one or more bases of the nucleotide sequence are modified by at least one of deletion, addition, insertion and substitution,
(e) a nucleotide which hybridizes with any one of the aforementioned nucleotides (a) to (d) under a stringent condition,
(f) a nucleotide which has homology with any one of the aforementioned nucleotides (a) to (d), and
(g) a nucleotide which is degenerate with respect to any one of the aforementioned nucleotides (a) to (f).

Example of the "stringent condition" is a condition in which the reaction system is incubated at a temperature of from 50 to 65° for a period of from 4 hour to overnight in 6×SSC (1×SSC is a solution composed of 0.15M NaCl and 0.015M citric acid, pH 7.0) containing 0.5% SDS, 5×Denhart's (a solution composed of 0.1% bovine serum albumin (BSA), 0.1% polyvinyl pyrrolidone and 0.1% Ficoll 400) and 100 μg/ml of salmon sperm DNA.

The GPO gene and the GPO gene after mutagenesis can also be prepared by chemical systhesis.

The GPO gene after mutagenesis is integrated into an appropriate vector such as pkk223-3 and transformed into a host such as E. coli and then the transformants are screened to select a transformant which can produce GPO having a modified property.

The genetic engineering as explained above can be carried out by utilizing the known methods as described in, for example, "Molecular Cloning, A Laboratory Manual" (edit. by T. Maniatis et al., Cold Spring Harbor Laboratory, 1989), etc., herein incorporated by reference.

When the thus obtained transformant is cultured using a nutrient medium, it stably produces a peptide having high GPO activity. Culturing of the transformant is carried out by selecting proper culturing conditions taking nutritional and physiological properties of the host into consideration, and in most cases, it is advantageous to carry out a liquid culturing in general or a submerged aeration agitation culturing for industrial purpose. The carbon source is any carbon compound which can be assimilated and, for example, glucose, lactose or maltose can be used. Also, the nitrogen source is any nitrogen compound which can be utilized, and yeast extract, peptone or meat extract can be used. The culturing temperature is within such a range that the modified GPO can be produced, and in the case of E. coli, it is preferably from about 20 to 42° C. The culturing is carried out for such a period of time that produced amount of the modified GPO becomes maximum, which is generally from 12 to 48 hours. The medium pH is controlled at such a level that the strain can be grown and the modified GPO can be produced stably, preferably at a pH of from 6 to 8.

The thus produced GPO can be treated in various ways depending on each purpose. When the modified GPO is produced inside the cells, the cells are collected by filtration, centrifugation or the like and disrupted by a physical method using a machine or an enzymatic method using an enzyme such as lysozyme or the like, thereby effecting extraction of the product. If necessary, the modified GPO obtained in this manner may be subjected to salting out, concentration, purification and the like.

According to the invention, method for the measurement GPO activity is as follows unless otherwise noted.

| Measuring method of GPO activity | |
| --- | --- |
| 100 mM | Potassium phosphate buffer (pH 7.0) |
| 300 mM | Sodium (±)-1-glycerophosphate n-hydrate |
| 5 u/ml | Peroxidase |
| 1.5 mM | 4-Aminoantipyrine |
| 0.05% | Triton X-100 |
| 1.0 mM | DAOS*[1] |

*[1]: 3,5-Dimethoxy-N-ethyl-N-(2-hydroxy-3-sulfopropyl)-aniline sodium salt

A 1.0 ml portion of a reaction solution having the above composition is put into a test tube and subjected to 5 minutes of preliminary incubation at 37° C., and then 20 μl of an enzyme solution is added thereto to carry out 5 minutes of the reaction at 37° C. After the reaction, 2.0 ml of 0.5% SDS solution is added to terminate the reaction, and calorimetric determination is carried out at a wavelength of 600 nm. An activity capable of forming 1 μmole of hydrogen peroxide within 1 minute was defined as 1 unit (U).

$$\text{Unit/mg} = \frac{\Delta A}{16.8 \times 1/2} \times \frac{3.02}{0.02} \times \frac{1}{X} \times \frac{1}{5}$$

16.8: Molar absorption coefficient of quinone pigment ($cm^2/\mu mol$)

X: Enzyme concentration (mg/ml)

The following describes the invention more illustratively with reference to examples, wherein the invention is not restricted by these examples but rather extends to a scope which can be easily modified by those skilled in the art.

EXAMPLE 1

<Cloning of Wild Type GPO Gene>

Using 300 ml of PYMG medium (1% polypeptone, 1% yeast extract, 0.5% meat extract, 1% glycerol, 0.2% sodium chloride, 0.1% potassium dihydrogenphosphate, 0.1% dipotassium hydrogenphosphate, 0.05% magnesium sulfate and 0.1% glucose, pH 9.0), *Enterococcus faecium* No. 7044 (FERM BP-7100) capable of producing GPO was cultured at 37° C. for 24 hours on a shaker, and the resulting cells were recovered by centrifugation.

The thus recovered cells were treated with lysozyme at 37° C. for 15 minutes and thoroughly mixed with 5 ml of 10% SDS solution and phenol saturated with TE (10 mM Tris-HCl (pH 8.0)+1 mM EDTA), and then the water layer (upper layer) was collected by centrifugation. After adding two volumes of ethanol, the DNA was coiled on a glass rod. The thus collected DNA was dissolved in the TE buffer to obtain chromosomal DNA of the wild type GPO-producing strain. A 5 $\mu$g portion of the thus obtained chromosomal DNA was partially digested with a restriction enzyme HindIII. A 1 $\mu$g portion of pSC423 (obtained by connecting a 3,030 bp fragment cut out from pSC101 using an HincII with a 1,789 bp fragment a 692 bp fragment which were cut out from pBR322 using an EcoT14I-DraI system and blunt-ended, contains an ampicillin resistance gene and a tetracycline resistance gene) was digested with HindIII and then subjected to dephosphorylation. Both of the DNA molecules were connected with each other using T4 DNA ligase (manufactured by Takara Shuzo), and *E. coli* TG1 was transformed using the thus obtained recombinant plasmid.

The thus obtained ampicillin resistant transformants were transferred on a sterilized #2 filter paper (manufactured by Advantech) which was then soaked in a lysozyme solution (10 mM EDTA, 0.1% Triton X-100, 50 mM phosphate buffer, 1 mg/ml lysozyme) to carry out 30 minutes of lysozyme treatment at 37° C.

After the lysozyme treatment, moisture was removed from the filter paper which was subsequently soaked in a GPO reaction solution (50 mM Tris-HCl pH 7.4, 200 mM NaCl, 0.01% aminoantipyrine, 1 mM phenol, 2 U/ml peroxidase, 300 mM sodium (±)-1-glycerophosphate n-hydrate) to carry out the reaction at 37° C., and then a transformant showing red color development around its colony was isolated.

The thus obtained transformant was inoculated into 5 ml of LA medium (1.0% tryptone, 0.5% yeast extract, 0.5% sodium chloride, 100 $\mu$g/ml ampicillin (pH 7.3)) and cultured at 37° C. for 16 hours on a shaker, and the resulting cells were collected and washed by centrifugation, subjected to lysozyme treatment and cell disruption and then centrifuged to obtain the supernatant. The supernatant showed a GPO activity of 1.5 units/ml.

A plasmid pGPO1 prepared from the thus obtained transformant contained an insertion DNA fragment of about 4.8 kb which is cut out with HindIII. As a result of trim down of the pGPO1, it was found that the GPO gene is present in a DNA fragment of about 3.2 kb which is cut out with EcoRI-HindIII. Next, a 5,383 bp EcoRI-HindIII fragment of pSC423 was connected with the GPO gene-containing 3.2 kb fragment to prepare pGPO97.

About 3.3 kb of insertion fragment of pGPO97 was digested with combinations of various restriction enzymes (EcoRI, ClaI, HindII, BGlII, PvuII and HindIII), and the thus subdivided fragments were cloned into pUC118 or pUC119. Kilo Sequence Kit and Deletion Kit (manufactured by Takara Shuzo) were used for the preparation of deletion plasmid.

Using plasmid DNA of each of the thus obtained clones, the reaction was carried out by the DNA Sequencing Kit manufactured by ABI, and the sequence of each fragment was determined by DNA Sequencer 373A, thereby obtaining complete nucleotide sequence of the 3.2 kb fragment. The insertion DNA fragment of pGPO97 was composed of 3,288 bases and contained only one open reading frame composed of 1,821 bases as the GPO gene.

The thus determined nucleotide sequence is shown as Sequence No. 2. Also, Sequence No. 1 shows amino acid sequence of polypeptide translated from the gene having nucleotide sequence of Sequence No. 2. The GPO gene contained a coding region of 1,821 bases and coded 607 amino acids.

EXAMPLE 2

<Modification of GPO Gene>

(1) Preparation of Template DNA

A fragment obtained by digesting pSC423 with EcoRI-EcoRV and then carrying out smooth-ending was connected with a 445 bp fragment obtained by digesting pUC19 with HaeII and then carrying out smooth-ending, thereby obtaining pSC442. The EcoRI-HindIII region of pSC442 was connected with the fragment of about 3.2 kb which contains the GPO gene and is cut out with EcoRI-HindIII, thereby preparing pGPO98.

(2) Mutagenesis of GPO Gene by PCR

The PCR reaction was carried out by mixing 5 $\mu$l (0.01 $\mu$g) of pGPO98 dissolved in TE buffer (pH 8.0) with 10 $\mu$l of five-fold concentration mutagenesis buffer [83 mM ammonium sulfate, 335 mM Tris-HCl (pH 8.8), 30.5 mM magnesium chloride, 33.5 $\mu$M EDTA (pH 8.0), 50 mM β-mercaptoethanol], 5 pmol of primers, 20 $\mu$l of dNTPs, 5 $\mu$l of DMSO and 2.5 U of DNA polymerase.

As the PCR primers, M13 primer RV and M13 primer M3 (manufactured by Takara Shuzo) were used.

| Conditions: | 96° C./1 minute | |
|---|---|---|
| | 95° C./30 seconds | |
| | 55° C./30 seconds | |
| | 72° C./3 minutes | 25 cycles |

The thus obtained PCR product was extracted with phenol and subjected to ethanol precipitation, the precipitate was dissolved and digested with restriction enzymes EcoRI and HindIII, and then the mutagenized GPO gene fragments were separated and recovered by agarose gel electrophoresis.

EXAMPLE 3

<Selection of Strains Containing Modified GPO Genes>

The mutagenized GPO gene fragments obtained in Example 2 were integrated into the EcoRI-HindIII site of pSC423 to carry out transformation of *E. coli* DH5. Colonies grown on an agar medium were checked for their enzyme activity by a replica method using a filter paper.

Colonies were replicated on a filter paper which was then soaked in a lysozyme solution prepared by adding lysozyme to 50 mM potassium phosphate buffer (pH 7.0) containing 10 mM EDTA and 0.1% Triton X-100, to a concentration of 1 mg/ml lysozyme, and incubated at 37° C. for 30 minutes. After the incubation, moisture was removed from the filter paper which was subsequently subjected to 60 minutes of heat treatment at 50° C. Next, this was soaked in a substrate mixture solution (50 mM Tris-HCl (pH 7.4), 200 mM NaCl, 0.01% 4-aminoantipyrine, 1 mM phenol, 2 U/ml peroxidase, 10 mM or 300 mM sodium (±)-1-glycerophosphate n-hydrate) and allowed to stand at 37° C. for 30 minutes, and then colonies having red color or showing red color on the filter paper around them were isolated.

Next, each of the strains selected by the above method was inoculated into 5 ml of LA medium (1.0% tryptone, 0.5% yeast extract, 0.5% sodium chloride, 100 μg/ml ampicillin (pH 7.3)) and cultured at 37° C. for 16 hours on a shaker, and the resulting cells were collected and washed by centrifugation, subjected to lysozyme treatment and cell disruption and then centrifuged to obtain respective supernatant. Each of the supernatants was checked for its GPO activity, Km value and heat resistance (residual activity after 30 minutes of heat treatment at 50° C.), thereby selecting 4 strains having property-improved mutant enzyme gene (Strains A14, D5, D6 and MT-2).

EXAMPLE 4
<Preparation of GPO>

Each of 4 transformants E. coli DH5/pGPOD5, DH5/pGPOD6, DH5/pGPOA14 and DH5/pGPOMT2 transformed with respective plasmid of colonies which showed color development by the method of Example 3 after mutagenesis of the GPO gene by the method of Example 2 was inoculated into 5 ml of LA medium and cultured at 37° C. for 8 hours on a shaker, and the culture broth was inoculated in an inoculum size of 5% into an ampicillin (200 μg/ml)-containing medium composed of 1.5% Polypeptone, 2.0% Meast P1G, 1.0% lactose, 0.3% dipotassium hydrogenphosphate and an appropriate amount of Adecanol (pH 7.2) and cultured at 37° C. for 16 hours on a shaker. The resulting cells were collected by centrifugation, washed with 10 mM Tris-HCl buffer (pH 8.0) containing 0.1 M sodium chloride and 1 mM EDTA and then suspended in a solution prepared by adding 1 mg/ml of lysozyme to 50 mM potassium phosphate buffer (pH 7.0) containing 10 mM EDTA and 0.1% Triton X-100, subsequently carrying out 2 hours of cell lysis at 4° C. After the cell lysis, this was subjected to ultrasonic disintegration and then centrifuged, and the supernatant was used as the enzyme solution to measure its enzyme activity, heat resistance and Km value.

EXAMPLE 5
<Purification of GPO>

Each of the enzyme solutions obtained by the method of Example 4 was treated with 40 to 70% saturation ammonium sulfate, and the resulting precipitate was recovered, dissolved in an appropriate buffer solution and then desalted and concentrated. Thereafter, this was adsorbed to Q-Sepharose or DEAE-Sepharose with a sodium chloride concentration of 0.2 M and then eluted with a sodium chloride concentration of 0.4 M to obtain an active fraction which was almost homogenous (purity 95% or more) based on electrophoresis.

EXAMPLE 6
<Determination of Nucleotide Sequence of Property-improved Mutant GPO Gene and Identification of Mutation>

Plasmid DNA was prepared from the property-improved mutant GPO gene, and nucleotide sequences of the gene fragments were determined by Sanger's dideoxy method, thereby revealing the mutation points and confirming changes in the amino acid sequence of the enzyme protein.

That is, the nucleotide sequence of wild type GPO gene of Enterococcus faecium and its corresponding amino acid sequence were compared with the nucleotide sequence of property-improved mutant GPO gene and its corresponding amino acid sequence, and their correlation with enzymatic properties was examined. As the results, the 130-position amino acid residue counting from the N-terminus was concerned in the affinity of GPO for substrate, the 225-position amino acid residue counting from the N-terminus in the Vmax of GPO, and the 298-position and 420-position amino acid residues counting from the N-terminus in the heat resistance of GPO.

In addition, improvement of two or more properties was found by a combination of these mutations. Comparison was made using E. coli DH5/pGPO97 (wild type GPO) as a control strain. The results are shown in Table 6. In the table, heat resistance was shown as residual activity (%) after 30 minutes of treatment at 50° C.

TABLE 6

| Mutation point | | | | Km value (mM) | Specific activity (U/mg protein) | Heat resistance (%) |
| --- | --- | --- | --- | --- | --- | --- |
| — | — | — | — | 23.2 | 17.8 | 16 |
| Phe 130 | — | — | — | 5.2 | — | 25.1 |
| — | Ala 225 | — | — | 23.8 | 41.2 | 16.2 |
| — | — | — | Gly 420 | 25 | — | 56.9 |
| Phe 130 | Ala 225 | — | — | 4.6 | — | 21.1 |
| Phe 130 | — | — | Gly 420 | 6.1 | — | 62.3 |
| — | Ala 225 | — | Gly 420 | 28.8 | — | 58.6 |
| Phe 130 | Ala 225 | — | Gly 420 | 7.8 | 6.22 | 94 |
| — | — | Pro 298 | — | 680 | 6.6 | 99 |
| Phe 130 | Ala 225 | Pro 298 | — | — | 6.6 | — |

EXAMPLE 7
<Introduction of Site-specific Mutation into GPO>

The 130-position leucine counting from the N-terminus, which is concerned in the affinity of GPO for substrate, was subjected to site-specific mutation to obtain substitution products in which this position was replaced by every amino acid. The site-specific mutation was carried out using TAKARA Mutan-Super Express Km. Each gene of the thus obtained substitution products was integrated into E. coli, and the GPO enzyme produced by each of the thus obtained transformants was checked for its GPO activity on the substrate in a low concentration (30 mM) and a high concentration (300 mM). Also, Km values were measured and compared on substitution products which showed high GPO activity at both substrate concentrations. As a result, when the position was replaced by an aromatic amino acid such as phenylalanine or tryptophan, the reactivity for low concentration substrate was improved and the heat resistance was also increased to about 3 times higher level.

TABLE 7

| Amino acid at the 130-position | GPO activity in different substrate concentration | | Relative ratio (%) 30 mM/300 mM | Residual activity (%) 50° C., 30 min. |
|---|---|---|---|---|
| | 30 mM | 300 mM | | |
| Ala | 4.8 | 17.7 | 27 | 15 |
| Ile | 37.6 | 192 | 20 | 8 |
| Val | 12 | 32.7 | 37 | 9 |
| Gly | 0.62 | 1.53 | 41 | — |
| Ser | 0 | 0 | — | — |
| Thr | 0.66 | 2.69 | 25 | — |
| Tyr | 0 | 0 | — | — |
| Cys | 6.6 | 25.3 | 26 | 12 |
| Met | 149 | 519 | 29 | 12 |
| Asp | 0 | 0.61 | — | — |
| Asn | 0.47 | 2.58 | 18 | — |
| Glu | 0.88 | 4.07 | 22 | — |
| Gln | 0.64 | 2.58 | 26 | — |
| Arg | 0 | 0 | — | — |
| Lys | 0 | 0.34 | — | — |
| His | 1.59 | 5.63 | 28 | — |
| Pro | 0 | 5 | — | — |
| Trp | 249 | 216 | 115 | 29 |
| Phe | 702 | 747 | 94 | 29 |
| Leu (wild type) | 227 | 909 | 25 | 10 |

Thus, as has been described in the foregoing, a novel GPO gene and a recombinant DNA containing the same are provided by the invention, and GPO can be produced efficiently by culturing a microorganism which contains the recombinant DNA and has the ability to produce GPO. Also, a GPO in which its properties such as affinity for substrate and heat resistance are improved by replacing an amino acid at a specified position by other amino acid and a method for its production are provided.

While the invention has been described in detail and with reference to specific embodiments thereof, it will be apparent to one skilled in the art that various changes and modifications can be made therein without departing from the spirit and scope thereof.

This application is based on a Japanese patent application No. Hei.-10-294674, filed on Sep. 30, 1998, incorporated herein by reference.

What is claimed is:

1. A polypeptide as set forth in SEQ ID NO: 1 exhibiting L-α-glycerophosphate oxidase activity, wherein the amino acid at position 130 of SEQ ID NO: 1 is replaced by another amino acid, and said polypeptide exhibits modified affinity for its substrate.

2. The polypeptide of claim 1, wherein the amino acid at position 130 of SEQ ID NO:1 is replaced by phenylalanine or tryptophan.

3. A polypeptide as set forth in SEQ ID NO: 1 exhibiting L-α-glycerophosphate oxidase activity, wherein the amino acid at position 298 of SEQ ID NO: 1 is replaced by another amino acid, and said polypeptide exhibits modified heat resistance.

4. The polypeptide of claim 3, wherein the amino acid at position 298 of SEQ ID NO:1 is replaced by proline.

5. A polypeptide as set forth in SEQ ID NO: 1 exhibiting L-α-glycerophosphate oxidase activity, wherein the amino acid at position 420 of SEQ ID NO: 1 is replaced by another amino acid, and said polypeptide exhibits modified heat resistance.

6. The polypeptide of claim 5, wherein the amino acid at position 420 of SEQ ID NO:1 is replaced by glycine.

7. A polypeptide as set forth in SEQ ID NO: 1.

8. A polypeptide which comprises a polypeptide having L-α-glycerophosphate oxidase activity and having an amino acid sequence as set forth in SEQ ID NO:1, wherein two to four amino acid residues selected from the group consisting of the amino acid at position 130, the amino acid at position 225, the amino acid at position 298, and the amino acid at position 420, are replaced by another amino acid.

9. The polypeptide of claim 8, wherein three to four amino acid residues selected from the group consisting of the amino acid at position 130, the amino acid at position 225, the amino acid at position 298, and the amino acid at position 420, are replaced by another amino acid.

10. The polypeptide of claim 8, wherein all four amino acid residues selected from the group consisting of the amino acid at position 130, the amino acid at position 225, the amino acid at position 298, and the amino acid at position 420, are replaced by another amino acid.

11. The polypeptide of claim 1, 3, or 5, wherein one to three additional amino acid residues of the amino acid sequence is modified by at least one of deletion, addition, insertion and substitution.

* * * * *